United States Patent [19]

Nilsson

[11] Patent Number: 4,896,068
[45] Date of Patent: Jan. 23, 1990

[54] ACTIVITY SENSOR FOR A HEART PACEMAKER

[75] Inventor: Kenth Nilsson, Akersberga, Sweden

[73] Assignee: Siemens Aktiengesellschaft, Berlin and Munich, Fed. Rep. of Germany

[21] Appl. No.: 346,342

[22] Filed: Apr. 28, 1989

Related U.S. Application Data

[63] Continuation of Ser. No. 97,139, Sep. 16, 1987, abandoned.

[30] Foreign Application Priority Data

Sep. 30, 1986 [DE] Fed. Rep. of Germany ....... 3633255

[51] Int. Cl.⁴ .................. H01L 41/08; A61N 1/00
[52] U.S. Cl. ................. 310/329; 128/419 PG;
 310/330; 310/338; 310/359; 310/366
[58] Field of Search ........ 310/319, 328, 329, 330–332,
 310/338, 339, 358, 359, 366; 128/419 P, 419 PS,
 419 PG, 419 B

[56] References Cited

U.S. PATENT DOCUMENTS

| | | | |
|---|---|---|---|
| 3,239,678 | 3/1966 | Kolm et al. | 310/339 |
| 3,456,134 | 7/1969 | Ko | 310/329 |
| 4,428,378 | 1/1984 | Anderson et al. | 128/419 PG |

OTHER PUBLICATIONS

Vibrit, Piezoceramic of Siemens, Order No. B–281/5035, pp. 19 and 20.

Primary Examiner—Mark O. Budd
Attorney, Agent, or Firm—Hill, Van Santen, Steadman & Simpson

[57] ABSTRACT

An activity sensor wherein a piezoelement of the flexural type is employed. The activity sensor avoids a depolarization even given great mechanical stresses and simplifies the contacting of such a sensor regardless of the surfaces to which it is applied. It is provided in accord with the invention that the piezoelement is composed of two individual or inter-related piezoceramic parts arranged side-by-side which are oppositely polarized and are provided with electrodes on both sides. On one side, the electrodes are electrically connected to one another and, on the other side, are connected to terminals.

5 Claims, 1 Drawing Sheet

ACTIVITY SENSOR FOR A HEART PACEMAKER

This is a continuation of application Ser. No. 097,139 filed Sept. 16,1987, now abandoned.

BACKGROUND OF THE INVENTION

The invention is directed to the field of activity sensors and, in particular, to an activity sensor for a heart pacemaker.

Piezoelectric activity sensors of the flexural type are known in the prior art (VIBRIT, piezoceramic of Siemens, Order No. N-281/5035, Pages 19 and 20). These sensors are composed of two piezoelectric wafers glued to one another which are usually oppositely polarized. Given this structure, the two exterior surfaces of the piezo-element are provided with an electrode. A center electrode also lies between the two wafers.

When this structure is bent, an electrical voltage arises between the two outer electrodes and is conveyed via terminals and serves as a measure for the activity acting on the piezo-element. The voltage is composed of a voltage via the upper piezoceramic wafer and of a voltage via the lower piezoceramic wafer. In one piezoceramic wafer, electrical voltage and polarization direction are isodirectional; in the other, by contrast, they are oppositely directed. These conditions can be understood when one considers that, when the piezoelement is bent, a mechanical tension arises, for example, in the upper piezoceramic wafer and, since the two wafers are joined, a pressure, i.e. a negative mechanical stress, thereby arises in the lower wafer.

It is known that piezoceramic can be depolarized on the basis of great mechanical stresses. The piezoceramic thereby entirely or at least partially looses its sensitivity as an activity sensor and becomes unusable for this application. The depolarization occurs in that the ceramic itself generates a correspondingly high electrical voltage given a great mechanical stress, this electrical voltage being directed opposite to the polarization. Given the above-described geometry, it is of no consequence in which direction the structure is bent. One of the generated electrical voltages will always be directed opposite the polarization in one of the wafers.

Alternatively, both piezoceramic wafers can be polarized in the same direction given such an activity sensor of the flexural type. In this case, the center electrode, i.e. the electrode between the two piezoceramic wafers, must be accessible for a connection. Usually, the two outer electrodes are interconnected and the voltage is taken between these and the center electrode. However, the output signal is thereby halved in comparison to a sensor having oppositely polarized piezoceramic wafers. At the same time, the capacitance becomes four times as high, so that the electrical energy remains constant. The risk of a mechanical depolarization is identical for both structures, regardless of the direction in which the structures are bent.

When the structure is to be always bent in only one direction, only one of the two piezoceramic layers can be utilized. The risk of a depolarization is thereby avoided. It is necessary, however, that the center electrode must be connected. This often represents a complication since this center electrode is frequently difficult to access. Here, too, only half the output signal derives and, over and above this, only half the electrical energy derives.

There is the further possibility that the piezoelement is composed of only a single piezoceramic wafer contacted at both sides and that this, for example, is glued to the inside wall of a heart pacemaker housing. Disadvantages corresponding to those in the two structures described above thereby occur.

A further disadvantage of all of these structures particularly derives when, for example, they are to be secured to a surface by gluing, as to the inside surface of a heart pacemaker housing. As long as this surface is conductive, there is the possibility of electrically connecting the electrode of the piezoelement that lies against this surface via the housing. When this electrode, however, is to be insulated from the housing or when the surface to which the piezoelement is glued is itself composed of insulating material, contacting difficulties arise.

SUMMARY OF THE INVENTION

The object of the present invention is to improve an activity sensor of the species initially cited such that a depolarization in all parts of the piezoelement is reliably avoided even given high mechanical stresses. Further, the invention is based on the object of significantly simplifying the contacting of such a sensor regardless of the surfaces to which it is to be attached.

Given the inventive structure of the activity sensor, electrical voltages are generated in the corresponding ceramic parts when this activity sensor is exposed to an external activity, these electrical voltages having the same direction in every part as the polarization prevailing therein. The risk of a depolarization is thereby suppressed even when this activity sensor is exposed to higher external forces or impacts. A further advantage is that the two terminals between which the electrical voltage is taken are situated at one side of the piezoelement. It thus becomes possible to glue this piezoelement to, for example, the inside of a heart pacemaker housing which thus directly serves as a carrier for the piezoelement. The piezoelement can also be insulated from the heart pacemaker housing or can even be directly applied to electrically insulating surfaces.

Given the employment of two ceramic parts, the output voltage between the terminals corresponds to the sum of the voltages in the two ceramic parts.

A further advantage of the activity sensor of the present invention is its higher sensitivity. In order to explain this in greater detail, the sensitivity is defined by way of example as the output voltage at the terminals divided by the force acting on the sensor. Let it be further assumed for the example that a ceramic part has the shape of a "board". Let it be further assumed that the mechanical flexural strength of this ceramic part is "one". When two such ceramic parts are arranged side-by-side as provided in the activity sensor of the present invention, then this structure has the flexural strength of 2.

When, as in the prior art, two ceramic parts are placed on top of one another and glued together, then a flexural strength having the value 8 derives for this structure.

This comparison shows that, given the structure of the present invention, a force lower by a factor of 4 is needed in order to bend the structure just as far as in the prior art. Given appropriate shaping, thus, the inventive structure can be made far more sensitive than the structures hitherto utilized.

The activity sensor of the invention thus unites the combination of the following advantages:

(a) High sensitivity;
(b) Easy of contacting; and
(c) Insensitivity to even great mechanical forces.

It is especially the latter property which assures that the piezoelement does not become depolarized and, thus, lose its sensitivity, which is particularly valuable in the employment of such a sensor in a heart pacemaker for which extremely high reliability is needed.

It is provided in a structurally advantageous development that the piezoelement is composed of a single plate whose surfaces are coated with electrodes, whereby an insulating gap is present on one side between these electrodes. Advantageously, the gap should thereby be at least twice as wide as the thickness of the piezoelement. The manufacture of the activity sensor is significantly simplified. First, a piezoceramic plate is provided with a continuous electrical layer on both sides and the electrical layer is subsequently removed in the region of the gap, this being done, for example, by grinding or etching. Subsequently, the ceramic parts can be simply polarized by applying an external voltage. A punch-through between the terminals is thereby reliably prevented on the basis of the selected gap width.

The small size of the sensor, its mechanical stability, high sensitivity and high reliability make it particularly suitable for employment in an implantable heart pacemaker and, in particular, at the inside of the heart pacemaker housing therein. The sensor output signal thereby represents a measure for the mechanical activities prevailing in the region of the heart pacemaker and can thus be used in a known way for the frequency control of the heart pacemaker.

It is provided in a further development of the invention that the flexural stiffness of the ceramic part is adapted to that of the mounting part to which it is secured. The force transmission between the mounting part and the sensor is thus optimized and its high sensitivity is therewith maximally exploited. Optimum conditions result when the boundary between the mounting part and the ceramic part thereby forms the "neutral surface", that is, the surface that retains its dimensions when the sensor is bent. The entire ceramic part is then stretched or compressed dependent on the bending direction. The piezoceramic and the mounting part thus, together, form the laminate required for a flexural transducer.

It is provided in an especially advantageous development of the invention that the electrical voltage generated in the activity sensor is additionally employable in a known way for operating electronic circuits. Particularly given an implantable heart pacemaker, the needed battery capacity is thereby reduced and, thus, the volume of the heart pacemaker is advantageously diminished. U.S. Pat. No. 3,456,134, for example, discloses how the output voltage of a piezoelement can be utilized for the voltage supply of the heart pacemaker electronics. In accordance with the present invention, the generated voltage is utilized twice, once for frequency control and once for voltage supply.

BRIEF DESCRIPTION OF THE DRAWINGS

The features of the present invention which are believed to be novel, are set forth with particularity in the appended claims. The invention, together with further objects and advantages, may best be understood by reference of the following description taken in conjunction with the accompanying drawings, in the several figures of which like reference numerals identify like elements, and in which:

DESCRIPTION OF THE PREFERRED EMBODIMENT

Figure 1:
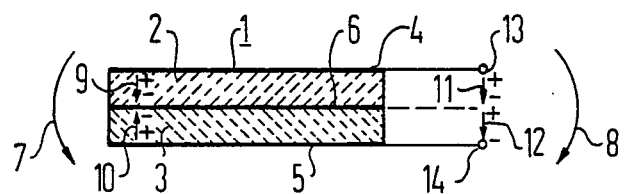
FIG. 1 is a cross-sectional view of a prior art activity sensor.

As shown in FIG. 1, a prior art activity sensor 1 is composed of two of two piezoceramic parts 2 and 3 which are glued on top of one another. Two outer electrodes 4 and 5 as well as a center electrode 6 are also provided. The arrows 9 and 10 indicate the polarization direction in the piezoceramic parts 2 and 3. The arrows 7 and 8 show the bending direction by way of example. The arrows 11 and 12 show the direction of the generated electrical voltage. The electrical voltage can be taken between the terminals 13 and 14, this electrical voltage corresponding to the sum of the voltage generated in the individual ceramic parts.

It can again be clearly derived from this FIG. 1 schematic that the electrical voltage generated in the ceramic part 3, as indicated by the arrow 12, is directed opposite to the polarization direction as indicated by the arrow 10. Thus, there is a risk of depolarization.

Figure 2:
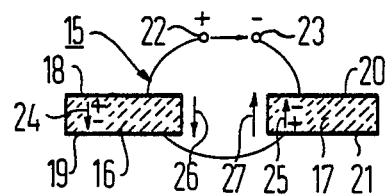
FIG. 2 is a cross-sectional view of a first embodiment of the activity sensor of the present invention.

FIG. 2 shows a first activity sensor 15 of the present invention wherein two ceramic parts 16 and 17 are arranged side-by-side. The surfaces of the two ceramic parts are again coated with electrodes 18, 19, 20 and 21. The electrodes 19 and 21 are electrically connected to one another. The electrodes 18 and 20 are connected to terminals 22 and 23, respectively. The polarization direction in the two ceramic parts is again indicated by arrows 24 and 25; the electrical voltage direction is likewise indicated by the arrows 26 and 27. As may be derived from FIG. 2, the electrical voltage always lies in the same direction as the polarization direction, so that a depolarization is avoided. Since the lower electrodes 19 and 21 are electrically connected to one another and need not be accessible for a terminal, this structure at the underside can be easily insulated or can be glued to an insulating surface without influencing the functioning of the sensor. The illustration of a carrier that forms the laminate of a flexural transducer together with the ceramic parts has been omitted in this FIG. 2.

Figure 3:
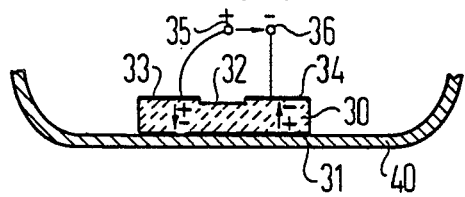
FIG. 3 is a cross-sectional view of an embodiment of the activity sensor for utilization in a heart pacemaker.

FIG. 3 shows another embodiment of the activity sensor of the invention. This sensor is composed of a piezoceramic plate or lamina 30 which has two parallel strips having opposite polarization. The underside of this piezoelement is connected to a through electrode 31; two electrodes 33 and 34 separated by a gap 32 are provided on the upper side. These electrodes are provided with terminals 35 and 36 between which the electrical voltage can be taken. The piezoelement is glued to the inside wall of a heart pacemaker housing 40 which is only partially shown here. The illustration of the further, known component parts of the heart pacemaker has been omitted for the sake of clarity.

Figure 4:
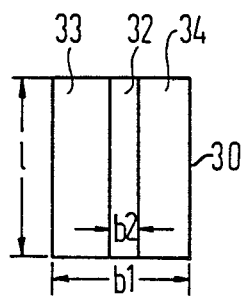
FIG. 4 is a plan view of the FIG. 3 sensor.

FIG. 4 shows a plan view of the FIG. 3 activity sensor by itself. The following dimensioning can thereby be provided for the employment in a heart pacemaker:

Width b1 of the piezoelectric lamina: approximately 5 mm,

Length 1 of the lamina: approximately 10 mm,

Width b2 of the gap: approximately 1 mm,

Thickness of the lamina: approximately 0.4 mm

Thickness of the electrode layers: approximately 0.003 mm

Figure 5:
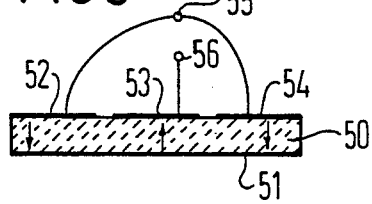
FIG. 5 is a cross-sectional view of a further embodiment of an activity sensor of the present invention.

FIG. 5 shows a further exemplary embodiment of an activity sensor wherein the piezoelement has three regions of different polarization. A single ceramic lamina 50 is again employed, this being provided with an electrode 51 at its underside and with three electrodes 52,53 and 54 at its upper side. The two electrodes 52, 54 belong to regions having polarization of the same direction and both are connected to a terminal 55. The region under the electrode 53 is polarized in the opposite direction. This electrode 53 is connected to a further terminal 56. The electrical voltage is then again taken between these two terminals.

The invention is not limited to the particular details of the apparatus depicted and other modifications and applications are contemplated. Certain other changes may be made in the above described apparatus without departing from the true spirit and scope of the invention herein involved. It is intended, therefore, that the subject matter in the above depiction shall be interpreted as illustrative and not in a limiting sense.

What is claimed is:

1. An activity sensor for use in a heart pacemaker having a housing with at least one flat wall, said activity sensor comprising:
   a flexural type piezoelement having oppositely polarized ceramic parts, each having first and second sides and contacted at both sides with electrodes, said ceramic parts being arranged side-by-side with said first sides facing said flat wall of said housing;
   means for electrically connecting said electrodes on said first sides of said ceramic parts to one another;
   means for securing said first sides in force-transmitting contact over entire area with said flat wall of said housing; and
   said electrodes on said second sides electrically connected to at least first and second terminals so that said piezoelement generates an electrical voltage across said terminals as a measure of activity acting upon the piezoelement through said wall of said housing.

2. The activity sensor according to claim 1, wherein said piezoelement is composed of a single plate having first and second sides, said electrodes on said second side having at least one insulating gap therebetween.

3. The activity sensor according to claim 2, wherein the width of the gap is at least twice as great as the thickness of the plate.

4. The activity sensor according to claim 1, wherein said means for securing is glue.

5. The activity sensor according to claim 1, wherein the activity sensor has a predetermined flexural strength relative to said wall of said housing to which the activity sensor is secured.

* * * * *